(12) United States Patent
Chang et al.

(10) Patent No.: US 9,144,551 B2
(45) Date of Patent: *Sep. 29, 2015

(54) DRUG FORMULATIONS HAVING REDUCED ABUSE POTENTIAL

(71) Applicant: Supernus Pharmaceuticals, Inc., Rockville, MD (US)

(72) Inventors: Rong-Kun Chang, Rockville, MD (US); Richard A. Couch, Chevy Chase, MD (US); Beth A. Burnside, Bethesda, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/563,089

(22) Filed: Dec. 8, 2014

(65) Prior Publication Data

US 2015/0150816 A1  Jun. 4, 2015

Related U.S. Application Data

(63) Continuation of application No. 10/435,597, filed on May 12, 2003, now Pat. No. 8,906,413.

(51) Int. Cl.
*A61K 9/14* (2006.01)
*A61K 9/20* (2006.01)
(Continued)

(52) U.S. Cl.
CPC .................. *A61K 9/2886* (2013.01); *A61K 9/14* (2013.01); *A61K 9/2013* (2013.01); *A61K 9/2018* (2013.01); *A61K 9/2853* (2013.01);
(Continued)

(58) Field of Classification Search
CPC ....... A61K 9/20; A61K 9/205; A61K 9/2013; A61K 9/28; A61K 9/2846
See application file for complete search history.

(56) References Cited

U.S. PATENT DOCUMENTS 3,079,303 A  2/1963  Raff et al.
3,383,283 A  5/1968  Brindamour
(Continued)

FOREIGN PATENT DOCUMENTS

EP  0 225 615 A2  6/1987
EP  1 382 331 A1  1/2004

OTHER PUBLICATIONS

Non-Final Office Action mailed on Apr. 7, 2009 in U.S. Appl. No. 11/250,309, 11 pages.
(Continued)

*Primary Examiner* — Lakshmi Channavajjala
(74) *Attorney, Agent, or Firm* — Foley & Lardner LLP; Sunit Talapatra

(57) ABSTRACT

Drug formulations having reduced abuse potential which contain one or more of (1) a bittering agent, (2) a bright deterrent/indicator dye and (3) fine insoluble particulate matter. The bittering agent and dye are in a form which does not affect proper administration of the drug, but the bittering agent creates a bitter side effect when the dosage form is crushed or chemically extracted and nasally, orally, buccally or sublingually administered and the dye produces a bright color when crushed and contacted. The fine insoluble particulate matter hinders extraction of the drug from the dosage form and, when crushed, can deter intravenous injection because of the presence of the insoluble particles or hinder injection by blocking an intravenous needle. The bright color of the dye, when extracted, also has a psychologically deterrent effect on intravenous abusers.

15 Claims, 1 Drawing Sheet

Mean Dissolution Profiles for Examples 4, 5, and 6

(51) Int. Cl.
*A61K 9/28* (2006.01)
*A61K 9/50* (2006.01)
*A61K 9/70* (2006.01)
*A61K 31/00* (2006.01)
*A61K 31/137* (2006.01)
*A61K 31/485* (2006.01)
*A61K 31/5513* (2006.01)
*A61K 47/18* (2006.01)
*A61K 47/22* (2006.01)
*A61K 47/26* (2006.01)
*A61K 47/34* (2006.01)
*A61K 47/38* (2006.01)

(52) U.S. Cl.
CPC .............. *A61K9/5078* (2013.01); *A61K 9/7061* (2013.01); *A61K 9/7069* (2013.01); *A61K 31/00* (2013.01); *A61K 31/137* (2013.01); *A61K 31/485* (2013.01); *A61K 31/5513* (2013.01); *A61K 47/186* (2013.01); *A61K 47/22* (2013.01); *A61K 47/26* (2013.01); *A61K 47/34* (2013.01); *A61K 47/38* (2013.01); *A61K 9/205* (2013.01); *A61K 9/2846* (2013.01); *A61K 9/5084* (2013.01)

(56) References Cited

U.S. PATENT DOCUMENTS

| | | |
|---|---|---|
| 4,070,494 A | 1/1978 | Hoffmeister et al. |
| 4,401,672 A | 8/1983 | Portoghese |
| 4,457,933 A | 7/1984 | Gordon et al. |
| 4,834,965 A | 5/1989 | Martani et al. |
| 5,162,341 A | 11/1992 | Cook |
| 5,236,714 A | 8/1993 | Lee et al. |
| 5,958,458 A | 9/1999 | Norling et al. |
| 6,124,282 A | 9/2000 | Sellers et al. |
| 6,159,501 A | 12/2000 | Skinhoj |
| 6,187,341 B1 | 2/2001 | Johnson et al. |
| 6,228,863 B1 | 5/2001 | Palermo et al. |
| 6,277,384 B1 | 8/2001 | Kaiko et al. |
| 7,141,250 B2 | 11/2006 | Oshlack et al. |
| 7,214,385 B2 | 5/2007 | Gruber |
| 8,906,413 B2 * | 12/2014 | Chang et al. .................. 424/489 |
| 2003/0064099 A1 | 4/2003 | Oshlack et al. |
| 2003/0064122 A1 | 4/2003 | Goldberg et al. |
| 2003/0091635 A1 | 5/2003 | Baichwal et al. |
| 2006/0018837 A1 | 1/2006 | Preston et al. |
| 2006/0083690 A1 | 4/2006 | Chang |

OTHER PUBLICATIONS

Matschiner et al. "Characterization of ion pair formation between erythromycin and lipophilic counter ions," Pharmazie, 1995, vol. 50, pp. 462-464.

Rao et al., "Effect of Sodium Lauryl Sulfate on the Release of Rifampicin from guar gum Matrix," Indian Journal of Pharmaceutical Sciences, Sep.-Oct. 2000, pp. 404-406.

Wells et al., "Effect of Anionic Surfactants on the Release of Chlorpheniramine Maleate from an Inert, Heterogeneous Matrix," Drug Development and Industrial Pharmacy, 1992, vol. 18, No. 2, pp. 175-186.

El-Kheshern et al., "Coating charcoal with polyacrylate-polymethacrylate copolymer for haemoperfusion III: The effect of the coat thickness on the adsorption capacity of the coated charcoal and its adsorptivity to small and middle size molecules," J. Microencapsulation, 1995, 12(5):505-514.

Final Office Action in U.S. Appl. No. 11/250,309 dated Sep. 24, 2012.

* cited by examiner

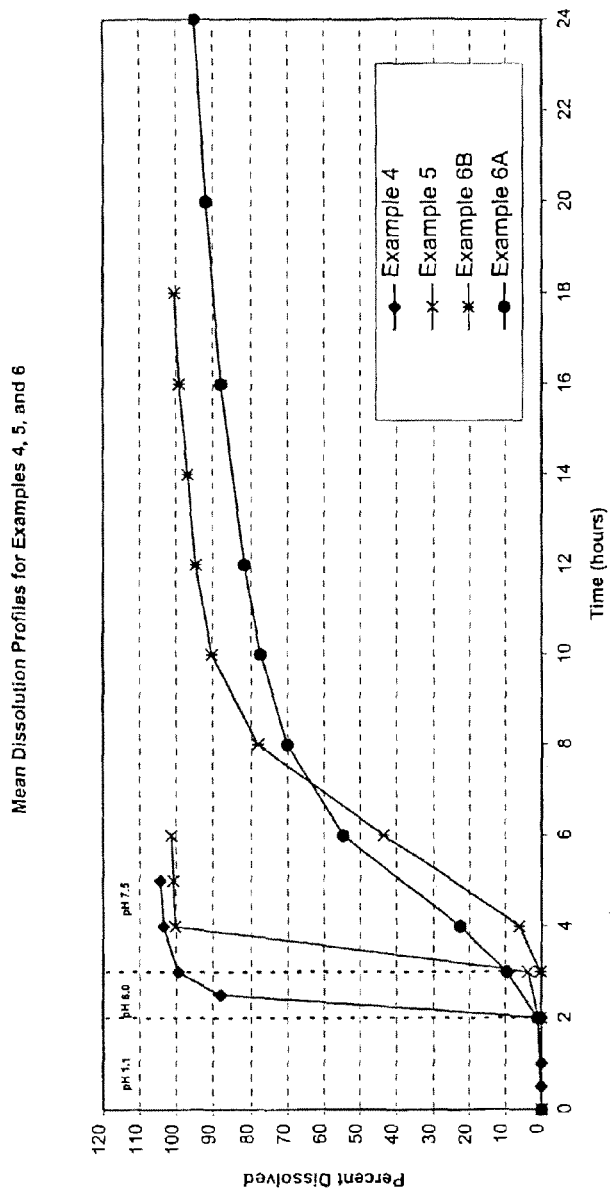

DRUG FORMULATIONS HAVING REDUCED ABUSE POTENTIAL

FIELD OF THE INVENTION

This invention relates to dosage forms of prescription psychoactive drug formulations having a reduced potential for abuse and to methods of reducing the potential for abuse of dosage forms of prescription psychoactive drugs.

BACKGROUND OF THE INVENTION

Prescription psychoactive drugs can help patients manage chronic or severe pain, restore emotional or behavioral balance, control sleep disorders, or fight obesity. When such prescription medications are abused, however, the consequences, including addiction, can be dangerous, even deadly. The risks associated with abuse of three classes of commonly abused prescription drugs, i.e., opioids; central nervous system (CNS) depressants, including sedatives and tranquilizers; and stimulants, are well documented.

Opioids include morphine, codeine, and related drugs such as oxycodone (Percodan and OxyContin), hydrocodone (Vicodin), and meperidine (Demerol) and are commonly prescribed to relieve pain. Taken as prescribed, opioids can be used to manage pain effectively without unwanted side effects. Chronic use of opioids can result in tolerance, which means that users must take higher doses to achieve the same effects. Long-term use can also lead to physical dependence and addiction. Withdrawal can occur when an individual discontinues use of the drugs. Withdrawal symptoms can include restlessness, muscle and bone pain, insomnia, diarrhea, vomiting, cold flashes with goose bumps, and involuntary leg movements. Individuals who are addicted to opioids are more likely to overdose on the drugs, which could be fatal.

Among the most commonly prescribed CNS depressants are barbiturates, such as mephobarbital (Mebaral) and pentobarbital sodium (Nembutal), which are prescribed to treat anxiety, tension, and sleep disorders; and benzodiazepines, such as diazepam (Valium) and alprazolam (Xanax), which typically are prescribed to treat anxiety, acute stress reactions, and panic attacks. Other benzodiazepines, such as triazolam (Halcion) and estazolam (ProSom), are prescribed for short-term treatment of sleep disorders. Although the various classes of CNS depressants work differently, they all produce a beneficial drowsy or calming effect in individuals suffering from sleep disorders or anxiety. However, if one uses these drugs over a long period of time, the body will develop tolerance, and larger doses will be needed to achieve the initial effects. In addition, continued use can lead to physical dependence and, when use is reduced or stopped, withdrawal. Both barbiturates and benzodiazepines have the potential for abuse and should be used only as prescribed. As with opioids, an overdose of these drugs can be fatal.

Stimulants increase heart rate, blood pressure and metabolism, provide feelings of exhilaration and energy, and increase mental alertness. Stimulants such as methylphenidate (Ritalin) and dextroamphetamine (Adderall and Dexedrine) are prescribed for the treatment of narcolepsy, attention-deficit/hyperactivity disorder, and depression that has not responded to other treatments. They also may be used for short-term treatment of obesity. Individuals may become addicted to the sense of well-being and enhanced energy that stimulants can generate. Taking high doses of stimulants repeatedly over a short time, however, can lead to feelings of hostility or paranoia. Additionally, taking high doses of stimulants may result in dangerously high body temperatures and an irregular heartbeat.

Abuse potential of these three classes of drugs is of major concern. This is specially true for opioids and stimulants and hence they are classified by the Drug Enforcement Agency (DEA) as Schedule II drugs (substances that have a high potential for abuse with severe liability to cause psychic or physical dependence, but have some approved medical use).

Various dosage forms of psychoactive drugs for medical use are available or possible. These include capsules, tablets, transdermal patches and liquid suspensions. For example, methylphenidate (Ritalin) is available in oral, tablet and extended-release tablet dosage forms. Dextroamphetamine (Adderall) is available in immediate-release tablet and extended-release capsule dosage forms. Methylphenidate, amphetamine, fentanyl, 3-methyl fentanyl, morphine, etorphine, etc. can be incorporated into transdermal patches. A fentanyl patch (Duragesic) is already in the marketplace and a methylphenidate patch (Methypatch) is under FDA review. Liquid suspensions of drugs in immediate release and sustained release forms are also possible. A sustained release system can be formulated by using drug ion-exchange complex particles with a further coating of ethyl cellulose. The ion-exchange technology makes reliable liquid controlled-release possible for many ionic drugs, which include amphetamine, methylphenidate, hydrocodone, codeine, morphine, and the like.

These various dosage forms provide valuable medical benefits when properly taken or administered, but also have a high potential for abuse. For example, sustained release dosage forms are abused by crushing or chewing and then swallowing or snorting or by mixing or dissolving in water or the like and then injecting. Transdermal patches can be chewed to provide a quick onset via buccal, sublingual, or oral absorption of the controlled substances. In addition, a significant drug residue after normal administration of the patches is quite common. Such residue can be extracted and concentrated for abuse. Liquid suspensions can be similarly concentrated and abused.

It view of these problems, new and improved dosage forms of psychoactive drugs having decreased abuse potential are desired. Several approaches to reducing the abuse potential of dosage forms of drugs can be found in U.S. patents. These include, for example, the incorporation of an opioid antagonist into a dosage form (U.S. Pat. Nos. 4,401,672, 4,457,933, 5,162,341, 5,236,714, 6,277,384 and 6,228,863), the use of cytochrome P450 2D6 enzyme inhibitor (U.S. Pat. No. 6,124,282), and the incorporation of a water soluble/gelable material into a dosage form (U.S. Pat. No. 4,070,494). However, these approaches still are far from ideal in terms of the effectiveness of deterring someone from abusing the medication by snorting or improper oral administration.

OBJECT OF THE INVENTION

It is an object of the present invention to reduce the potential for abuse of dosage forms of psychoactive drugs and other drugs of abuse and to provide dosage forms of psychoactive drugs having a reduced potential for abuse. More particularly, it is an object of the present invention to provide oral dosage forms of opioids, CNS depressants and stimulants that have increased effectiveness in deterring abuse by snorting/injecting or the like.

SUMMARY OF THE INVENTION

According to the present invention dosage forms of psychoactive drugs, which have reduced abuse potential are provided by adding one or more of the following to the dosage forms:

(1) a bittering agent in a form which does not create a bitter taste when a dosage form of the drug is properly administered, but which creates a bitter side effect when the dosage form is crushed or chemically extracted for nasal (snorting), oral, buccal or sublingual administration;

(2) a bright deterrent/indicator dye in a form which does not create color when a dosage form of the drug is properly administered, but which colors or stains the nose, mouth or hands when the dosage form is crushed or chemically extracted; and (3) fine insoluble particulate matter which does not adversely affect the human body when a dosage form of the drug is properly administered, but which hinders extraction of the drug from the dosage form and can deter intravenous injection because of the presence of the insoluble particles or hinder injection by blocking the intravenous needle.

BRIEF DESCRIPTION OF THE DRAWING

The drawing is a graph showing the mean dissolution profiles of the drug formulations prepared in Examples 4, 5 and 6.

DETAILED EXPLANATION OF THE INVENTION

The psychoactive drug (i.e., a drug that affects the central nervous system) of the dosage form of the present invention is not particularly limited insofar as the drug is approved for medical use in dosage form and has a potential for abuse. The drug includes opioids, central nerve system (CNS) depressants and stimulants such as, for example, drugs sold commercially under the trademarks Adderall XR, Matadate CD, Kadian, Oramorph SR, MS Contin, Oxycontin and the like.

The bittering agent and/or indicator dye to be incorporated into the dosage forms of the present invention is used in a form which does not exhibit its deterrent effect when a dosage form of the drug is properly administered, but exhibits a deterrent effect when the dosage form is chewed, crushed or chemically extracted for nasal (snorting), oral, buccal or sublingual administration. The bittering agent and/or indicator dye can be incorporated into granules, beads, or mini-tablets which can be subsequently coated with a suitable barrier coating to prevent against leakage of the bittering agent and indicator dye and to minimize or prevent absorption of the bittering agent and indicator dye under normal dosage administration conditions. These granules/beads/mini-tablets can be encapsulated or compressed with the drug of interest or can be used as coating substrates for drug layering and further enteric/sustained-release coatings.

The sizes of the granules, beads and mini-tablets is not limited as long as the granules can be incorporated into the dosage forms of the invention. Typically, the granules and beads have a size of 50 μm to 4000 μm. The mini-tables have a size which is typically significantly smaller than common tablets (<9/32 inch diameter). When granules, beads or mini-tablets containing a bittering agent and/or a dye indicator and not containing a drug are encapsulated with granules, beads or mini-tablets containing an active pharmaceutical ingredient (API), the granules, beads or mini-tablets are preferably of the same size to make it difficult for the respective beads to be distinguished and separated.

Alternatively, the bittering agent and/or indicator dye can be incorporated directly into a drug formulation and the resultant formulation incorporated into granules, beads, or mini-tablets. Subsequently, a barrier coating is applied to ensure against leakage of the bittering agent and indicator dye under normal dosage administration conditions. The resultant coated granules, beads or mini-tablets of the drug formulation are thereafter encapsulated or compressed into tablets.

When used in a transdermal patch formulation, the bittering agent and/or indicator dye can be used in the form of the above-described granules, beads, or mini-tablets coated with a suitable barrier coating. The bittering agent can also be added directly to the transdermal drug formulation.

The bittering agent useful in the present invention includes any pharmaceutically acceptable bitter substance that creates a bitter taste or side effect when administered nasally (snorted), orally, bucally or sublingually. Such agents include, but are not limited to, sucrose octaacetate, denatonium saccharide, denatonium benzoate, caffeine, quinine (or a quinine salt such as quinine sulfate), bitter orange peel oil, and other botanical extract ingredients, such as pepper extract (Cubeb), capsicum, and the like. The preferred bittering agents are sucrose octaacetate, denatonium saccharide and denatonium benzoate because they are inexpensive, show an unusually pronounced bitter tasting effect at low concentrations and are essentially non-toxic in the low concentrations used in the drug formulations of the invention.

Sucrose octaacetate is a USP/NF material and is an intensely bitter compound and has been used in the industry as a bittering agent or a denaturant for alcohol. Denatonium benzoate is the chemical name for Bitrex, an exceptionally bitter substance, which has been added to appropriate home care products. Denatonium saccharide is reportedly four times more bitter than denatonium benzoate. When a product contains sucrose octaacetate, denatonium benzoate or denatonium saccharide, it has such an intensely nasty taste it is practically impossible for a person to ingest it.

The bittering agent is used in an amount of from 0.01 to 10% by weight and, preferably, 0.1 to 4% by weight and, most preferably, 0.1 to 0.5% by weight based on the weight of a dosage form of the pharmaceutical formulation into which the agent is incorporated.

The indicator dye useful in the invention includes any dye that is pharmaceutically acceptable and that is capable of providing an intense, bright color on the nose, mouth and hands after a pharmaceutical formulation containing the dye is crushed or dissolved. The bright color also can have a psychologically deterrent effect on intravenous abusers. Such dyes include, but are not limited to allura red, amaranth, brilliant blue, canthaxanthin, carmine, carmoisine, carotene, curcumin, erythrosine, green S, indigo carmine, iron oxide black, iron oxide red, iron oxide yellow, patent blue, phloxine O, ponceau 4R, quinoline yellow, riboflavin, sunset yellow, tartrazine, titanium dioxide, vegetable carbon black, and other natural colors such as annatto, beet, black carrot, black currant, caramel, carmine, carmine lake, chlorophyll, cochineal, elderberry, grapeskin/grape juice, malt, paprika, red cabbage, turmeric, and anthocyanins. Riboflavin is a preferred indicator because it can also be used as a tracing agent for easy urine detection of drug abusers.

The amount of the dye indicator used in the dosage form of the pharmaceutical formulation will vary with the particular dye used but, typically, the dye indicator is used in an amount of 0.01 to 20% by weight and, preferably, 0.1 to 10% by weight, and, most preferably, 0.1 to 5% by weight, based on the weight of a dosage form of the pharmaceutical formulation.

The granules, beads, mini-tablets and tablets of the bittering agent and/or dye indicator and of the drug formulations containing the bittering agent and/or dye indicator can be made by various known pharmaceutical processes, such as roller compacting, and solution/slurry/powder layering in a fluid bed or other appropriate coating equipment, and compressing in a tablet press. In a particularly preferred embodiment, core seeds such as non-pareil seeds are coated with a layer of the bittering agent and/or dye indicator and a barrier coating is applied to the layered core seeds.

The barrier coating applied to the granules, beads or mini-tablets containing the bittering agent and/or dye indicator or to granules, beads, mini-tablets or tablets of drug formulations containing the bittering agent and/or dye indicator to minimize or prevent leakage of the agent and dye and to minimize absorption of the agent and dye under normal conditions of dosage administration can be a protective coating, enteric coating or sustained release coating or various combinations of these coatings. In a preferred embodiment, granules, beads or mini-tablets containing the bittering agent and/or dye indicator and not containing the drug are coated with a non-dissolving pharmaceutically acceptable polymer coating which does not dissolve or release under conditions existing in the GI tract. With such a coating, the bittering agent and/or dye indicator is not released in the human body when properly administered and is released only when a drug formulation including the granules, beads or mini-tablets coated with the non-dissolving coating is crushed for non-prescribed purposes.

The barrier coating may be applied by conventional coating techniques such as pan coating or fluid bed coating using solutions of polymers in water or suitable organic solvents or by using aqueous polymer dispersions.

Materials useful as a protective coating are well-known in the art and include, for example, cellulose derivatives such as hydroxyethyl cellulose, hydroxypropyl cellulose, hydroxypropyl methylcellulose, polyvinylpyrrolidone, polyvinylpyrrolidone/vinyl acetate copolymer, and pH dependent cationic polymers soluble in gastric fluid up to pH 5.0 such as those sold under the trademarks EUDRAGIT E 100 and EUDRAGIT EPO. The suggested coating levels are from 1 to 6%, preferably 2-4% (w/w).

The enteric coating layer can be any pH-sensitive polymer, which dissolves at a pH greater than 4.5, after a certain delayed time, or after the coated unit passes through the stomach. The preferred delay time is in the range of two to six hours. Suitable enteric polymers include cellulose acetate phthalate, cellulose acetate trimellitate, hydroxypropyl methylcellulose phthalate, polyvinyl acetate phthalate, carboxymethylethylcellulose, and co-polymerized methacrylic acid/methacrylic acid methyl esters such as, for instance, materials sold under the trademarks EUDRAGIT L100, EUDRAGIT L100-55, EUDRAGIT L 30 D-55 or EUDRAGIT S100 or similar compounds used to obtain enteric coatings. The suggested coating levels are from 1 to 6%, preferably 2-4% (w/w).

The enteric polymers can be modified by mixing with other known coating products that are not pH sensitive to provide sustained controlled release. Examples of such coating products include the neutral methacrylic acid esters with a small portion of trimethylammonioethyl methacrylate chloride, sold currently under the trademarks EUDRAGIT RL 30 D, EUDRAGIT RL PO, EUDRAGIT RL 100, EUDRAGIT RS 30 D and other pH independent coating products.

The pharmaceutically acceptable coating that does not dissolve in the GI tract includes cellulose acetate, cellulose acetate butyrate, cellulose acetate propionate, ethyl cellulose, poly(ethyl acrylate), poly (methyl methacrylate), and poly (trimethylammonioethylmethacrylate chloride). Suitable coating levels are those that prevent premature leakage of the bittering/coloring (dye) agent and depend on the coating used. Coating levels range, for example, from 1 to 60% (w/w).

An overcoating layer can further optionally be applied to the composition of the present invention. OPADRY®, OPADRY II® (sold by Colorcon) and corresponding color and colorless grades from Colorcon can be used to protect the pellets from being tacky and to provide color to the product. Additionally, Kollicoat IR (sold by RASF) with or without colorants and opacifiers can be used as an overcoating layer. The suggested levels of protective or color coating are from 1 to 6%, preferably 2-3% (w/w).

In an alternative embodiment, insoluble particulate matter is used in the pharmaceutical formulations to hinder drug abusers from extracting the drug from the dosage units, to deter drug abusers, because of the insoluble particulate matters, from injecting the formulations intravenously, and to hinder the injection because of needle blocking. Suitable fine solid particulate materials include, but are not limited to, Noveon® AA-1 polycarbophil, Ethocel® FP, methacrylic acid copolymer (e.g., Eudragit® L100-55, Eudragit® S100), microcrystalline cellulose (e.g., Avicel® PH 102), sodium starch glycolate, crospovidone, croscarmellose sodium, talcum, and silicon dioxide. The size of the particles is selected such that the particles are easily suspended in the extraction media to hinder the extraction and block a needle while injecting. The usual particle size is from 1 µm to 150 µm and, preferably, from 1 µm to 50 µm.

The insoluble fine particles can be included in the deterrent granules, beads or mini-tablets that contain the bittering agent and/or the dye indicator with or without the drug of interest. Alternatively, the insoluble fine particles can be encapsulated or compressed with the drug-containing granules, beads or mini-tablets.

The water-insoluble agent is used in an amount of from 5 to 80% by weight and, preferably, from 5 to 40% by weight, and, most preferable, from 5 to 10% by weight, based on the weight of a dosage form of the pharmaceutical formulation into which the agent is incorporated.

EXAMPLES

The following examples are presented to illustrate embodiments of the invention. The invention, however, is not limited to these embodiments but, instead, includes all those embodiments within the spirit and scope of the intended claims.

Example 1

The formulation in Table 1 is used to layer a bittering agent (sucrose octaacetate) and an indicator dye (tartrazine) onto sugar spheres. Nonpareil seeds (30/35 mesh, Paulaur Corp., NJ), 6.8 kg are put into a Glatt GPCG-15 fluid bed processor with a 9" Wurster column and fluidized at 60° C. The coating system containing sucrose octaacetate, tartrazine, and HPMC E5 Premium (Dow Chemical) as a binder is sprayed onto the seed under suitable conditions. Almost no agglomeration and no fines is observed with a yield of at least 98%. Subsequently, a barrier coat is applied onto the sucrose octaacetate and tartrazine loaded beads to ensure no leakage of the bittering agent and tartrazine dye and to minimize the absorption of these agents in the gastrointestinal tract.

The procedure described above can be used to prepare beads loaded with either sucrose octaacetate or tartrazine and other bittering agents and other dyes can be substituted for the sucrose octaacetate and tartrazine.

TABLE 1

| Ingredients | Amount (%) |
| --- | --- |
| Non-pareil seeds | 89.4 |
| Sucrose octaacetate | 5.0 |
| Tartrazine | 5.0 |
| Methocel ® E5 Premium | 0.6 |
| Water | * |

* removed during processing

Example 2

The formulation in Table 2 is used to coat the beads from Example 1 with Eudragit® E100 and subsequently with Eudragit®FS30D. 3.6 kg of beads (contain sucrose octaacetate and tartrazine) are loaded into a fluid bed processor with a Wurster column equipped with an HS nozzle (GPCG-15, Glatt Air Techniques). The Eudragit® E100 spray suspension is prepared by dispersing talc and dissolving the Eudragit® E100 in the organic solvent system (acetone:isopropyl alcohol 50:50). Under suitable fluidization conditions, the coating system is sprayed onto the fluidized pellets. Subsequently, a coating dispersion is prepared by dispersing triethyl citrate, talc and EUDRAGIT® FS 30D into water and mixing for at least 30 minutes. Under suitable fluidization conditions, the coating dispersion is sprayed onto the fluidized Eudragit® E100 coated beads. The spraying is continued until the targeted coating level is achieved (20 µm). The coated beads are dried at 30-35 C. for 5 minutes before stopping the process. Talc is added to the Eudragit® FS30D coated beads to minimize the static charge and to prevent the agglomeration of the beads. The enteric coated beads are tested in acidic medium and no leakage of the bitter agent and coloring agent is observed. The beads from this example can be encapsulated with sustained-release beads, immediate-release beads, delayed-release beads, or the combination of any of these types of beads. Also, the beads from the Example 2 can be compressed with sustained-release or immediate-release matrix tablet formulation to reduce the abuse potential.

TABLE 2

| Ingredient | Amount (%) |
| --- | --- |
| Beads containing sucrose octaacetate and tartrazine | 62.0 |
| Eudragit ® E100 | 5.0 |
| Talc | 1.0 |
| Acetone | * |
| Isopropyl alcohol | * |
| Eudragit ® FS30D | 26.24 |
| Triethyl citrate | 0.76 |
| Talc | 3.0 |
| Water | * |
| Talc** | 2.0 |

* removed during processing
**Talc was used to dry blend with beads to minimize the static charge and to prevent the agglomeration during the storage.

Example 3

The formulation in TABLE 3 is used to layer mixed amphetamine salts onto sugar spheres. Nonpareil seeds (30/35 mesh, Paulaur Corp., NJ), 6.8 kg are put into a Glatt GPCG-15 fluid bed processor with a 9" Wurster column and fluidized at 60° C. The suspension of mixed amphetamine salts with 1% HPMC E5 Premium (Dow Chemical), sucrose octaacetate and tartrazine is sprayed onto the seed under suitable conditions. Almost no agglomeration and no fines are observed with a yield of at least 98%. The drug-loaded cores are coated with enteric and sustained release coatings.

TABLE 3

| Ingredients | Amount (%) |
| --- | --- |
| Nonpareil seed | 82.00 |
| mixed amphetamine salts | 11.40 |
| METHOCEL ® E5 Premium | 0.60 |
| Sucrose octaacetate | 3.0 |
| Tartrazine | 3.0 |
| Water | * |

* removed during processing

Example 4

The formulation in Table 4 is used to coat the beads coated with mixed amphetamine salts from Example 3 with the EUDRAGIT® L 30D-55 (Rohm Pharma, Germany) coating dispersion. 3.6 kg of amphetamine beads are loaded into a fluid bed processor with a Wurster column equipped with an HS nozzle (GPCG-15, Glatt Air Techniques). The coating dispersion is prepared by dispersing triethyl citrate, talc and EUDRAGIT® L 30D-55 into water and mixing for at least 30 minutes. Under suitable fluidization conditions, the coating dispersion is sprayed onto the fluidized mixed amphetamine salt loaded (MASL) beads. The spraying is continued until the targeted coating level is achieved (20 µm). The beads are further coated with OPADRY® beige to prevent agglomeration during storage. The enteric coated amphetamine pellets are tested at different pH buffers by a USP paddle method. The drug content is analyzed using HPLC. The mean dissolution profile for the pellets is shown in the drawing. The results show that the enteric coating delays the drug release from the coated beads until after exposure to pH 6 or higher.

TABLE 4

| Ingredients | Amount (%) |
| --- | --- |
| Amphetamine beads from Example 3 | 68.10 |
| EUDRAGIT ® L 30D-55 | 24.78 |
| Triethyl citrate | 2.52 |
| Talc | 2.60 |
| OPADRY ® beige | 2.0 |
| Water | * |

* removed during processing

Example 5

The formulation in Table 5 is used to coat the amphetamine beads from Example 3 with EUDRAGIT® FS30D (Rohm Pharma, Germany) coating dispersion. The amphetamine beads (3.6 kg) are loaded in a fluid bed processor with a Wurster column (GPGC-15, Glatt). The coating dispersion is prepared by dispersing triethyl citrate, talc and EUDRAGIT® FS30D into water and mixing for at least 30 minutes. Under suitable fluidization conditions, the coating dispersion is sprayed onto the fluidized amphetamine beads. The spraying is continued until the targeted coating level is achieved. The coated beads are dried at 30-35° C. for 5 minutes before stopping the process. The enteric coated amphetamine beads are tested using a USP paddle method at different pH buffers. The drug content is analyzed using HPLC. The mean dissolution profile for the beads is shown in the drawing. The enteric coating delays the drug release from the coated beads for several hours until the pH value reaches 6.8 or higher.

TABLE 5

| Ingredients | Amount (%) |
| --- | --- |
| Amphetamine pellets from Example 3 | 65.50 |
| EUDRAGIT ® FS30D | 24.38 |
| Triethyl citrate | 1.35 |
| Talc | 6.77 |
| OPADRY ® white | 2.00 |
| Water | * |

* removed during processing

Example 6

The formulation in Table 6 is selected to coat enteric coated amphetamine beads. Coated amphetamine beads from Example 4 (Example 6A) or coated amphetamine beads from Example 5 (Example 6B) (4.3 kg) are loaded into a fluid bed processor with a reduced Wurster column (GPCG-15, Glatt). The coating dispersion is prepared by mixing SURELEASE (Colorcon) and water for at least 15 minutes prior to spraying. Under suitable fluidization conditions, the coating dispersion is sprayed onto the fluidized beads. The spraying is continued until the targeted coating level is achieved. The coated beads are blended with talc (2%) to minimize the static charge and to prevent tackiness of the coated beads during storage. The coated beads are then dried at 35-40° C. for 10 minutes before discharging from the bed. The drug dissolution from both coated beads is performed using a USP paddle method at different pH buffers. The drug content is analyzed using HPLC. The mean dissolution profile for the beads is shown in the drawing. The 12% SURELEASE® coating slightly sustains the drug release from both EUDRAGIT® L 30D-55 and EUDRAGIT® FS30D coated beads at pH 7.5 buffer, while the EUDRAGIT® coating delays the drug release up to 2 hours after the buffer switches from pH 1 to pH 7.5.

TABLE 6

| Ingredients | Amount (%) |
| --- | --- |
| Enteric coated amphetamine beads from Example 4 or 5 | 86.00 |
| SURELEASE ® | 12.00 |
| Water | * |
| Talc** | 2.00 |

* removed during processing
**Talc was used to dry blend with beads to minimize the static charge and to prevent the agglomeration during the storage.

Example 17

The formulation in Table 7 is used to layer morphine sulfate onto sugar spheres. Nonpareil seeds (30/35 mesh, Paulaur Corp., NJ), 6.8 kg, are put into a GPCG-15 fluid bed processor with a 9" Wurster column and fluidized at 60° C. The suspension of a drug with abuse potential with 1% HPMC E5 Premium (Dow Chemical) as a binder is sprayed onto the seed under suitable conditions. Almost no agglomeration and no fines are observed with a yield of at least 98%. The drug-loaded cores are optionally used as substrates to prepare products coated with enteric and/or sustained release coatings similar to those in Examples 4, 5 and 6. The immediate-release beads obtained from Example 7, the delayed-release beads (beads from Example 7 further coated with enteric material), the sustained-release beads (beads from Example 7 further coated with sustained-release material), and any combination of beads can be encapsulated with beads from Example 10 to reduce the abuse potential.

TABLE 7

| Ingredients | Amount (%) |
| --- | --- |
| Nonpareil seed | 87.90 |
| Morphine sulfate | 11.40 |
| METHOCEL ® E5 Premium | 0.6 |
| Water | * |

* removed during processing

Example 8

Tablet Formulation of a High Potency Compound

Blend the first three powders shown in Table 8 in a V-Blender for 10 minutes. Add clonazepine (or triamcinolone, pergolide, etc.), tartrazine and denatonium benzoate to the powder blend and blend for an additional 10 minutes with the intensifier bar on. Add magnesium stearate to the mix and blend for an additional 2 minutes. Press tablets on a conventional or other rotary tablet press to give 200 mg tablet weight.

TABLE 8

| Ingredients | Amount (%) |
| --- | --- |
| Lactose | 45.94 |
| Microcrystalline cellulose | 46.95 |
| Acdisol | 2.0 |
| Mag Stearate | 1.0 |
| Clonazepine | 0.005 |
| Bitrex | 0.1 |
| Tartrazine | 3.0 |

Example 9

The following formulation is used to coat the core tablet from Example 8 for taste masking purpose. The coating solution is prepared by dissolving the EUDRAGIT® E100 in a solvent system (acetone:isopropyl alcohol 50:50). The coating process is carried out in a side-vented coating pan.

TABLE 9

| Ingredients | Amount (%) |
| --- | --- |
| Core Tablet from Example 8 | 70.0 |
| EUDRAGIT ® E100 | 30.0 |
| Acetone | * |
| Isopropyl alcohol | * |

* removed during the process

Example 10

This example illustrates preparation of a sustained release formulation using a procedure similar to Example 8. Blend Polyvox, microcrystalline cellulose, magnesium stearate and morphine sulfate (see Table 10) in a V-Blender for 10 minutes.

Add morphine sulfate, indigo carmine, and denatonium benzoate and blend for an additional 10 minutes with the intensifier bar on. Add magnesium stearate to the mix and blend for an additional 2 minutes. Press tablets on a conventional or other rotary tablet press to give 75 to 500 mg tablets, depending on desired dose (e.g., 15 mg, 30 mg, 60 mg, and 100 mg strength). The core tablets produced are coated with EUDRAGIT® E100 (see Example 17) for taste masking purpose.

TABLE 10

| Ingredients | Amount (%) |
|---|---|
| Polyox | 40.0 |
| Microcrystalline Cellulose | 45.8 |
| Magnesium Stearate | 1.0 |
| Morphine sulfate | 20.0 |
| Bitrex | 0.2 |
| Indigo Carmine | 3.0 |

Example 11

The following formulation is used to layer the bittering agent (denatonium saccharide) and the indicator dye (tartrazine) onto sugar spheres. Nonpareil seeds (30/35 mesh, Paulaur Corp., NJ), 6.8 kg are put into a Glatt GPCG-15 fluid bed processor with a 9" Wurster column and fluidized at 60° C. The coating system containing denatonium saccharide, tartrazine, and HPMC E5 Premium (Dow Chemical) as a binder is sprayed onto the seed under suitable conditions. Almost no agglomeration and no fines are observed with a yield of at least 98%.

TABLE 11

| Ingredients | Amount (%) |
|---|---|
| Nonpareil seed | 89.4 |
| Denatonium saccharide | 5.0 |
| Tartrazine | 5.0 |
| Hydroxypropyl methyl cellulose | 0.6 |
| Water | * |

* removed during processing

Example 12

The following formulation is used to coat the beads from Example 11 with cellulose acetate as a barrier coat to ensure against leakage of the bittering agent and tartrazine dye and to minimize the absorption of these agents in the gastrointestinal tract. 3.6 kg of the beads are loaded into a fluid bed processor with a Wurster column equipped with an HS nozzle (GPCG-15, Glatt Air Techniques). Cellulose acetate and triethyl citrate are dissolved in an organic solvent system (acetone:isopropyl alcohol 80:20). Under suitable fluidization conditions, the coating system is sprayed onto the fluidized pellets. The beads from this example can be encapsulated with sustained-release beads, immediate-release beads, delayed-release beads, or the combination of any of these types of beads. Also, the beads can be compressed with a sustained-release or immediate-release matrix tablet formulation to reduce the abuse potential.

TABLE 12

| Ingredients | Amount (%) |
|---|---|
| Beads from Example 11 | 70.0 |
| Cellulose acetate | 27.0 |
| Triethyl citrate | 3.0 |
| Acetone:isopropyl alcohol (80:20) | * |

* removed during processing

Insoluble fine particles can be added to the formulations of Examples 1, 3, 7 and 8 to obtain beads containing a bittering agent, dye indicator and insoluble fine particles of drug loaded beads containing API (active pharmaceutical ingredient) and insoluble fine particles. Alternatively, the insoluble fine particles can be encapsulated or compressed with coated granules, beads or mini-tablets or drugs of interest.

Example 13

This example describes the preparation of a transdermal patch dosage form of the invention. A methylphenidate-polymer mixture is prepared by combining 20 parts of methylphenidate, 1 part of sucrose octaacetate, 1 part of tartrazine, 1.3 parts of lecithin, 1 part of propylene glycol, 1 part of dipropylene glycol, 0.8 part of oleic acid, 2.5 parts of polydimethylsiloxane, 28.6 parts of polyacrylate, and 42.8 parts of polysiloxane, and mixed well in an appropriate container (see Table 13). Methylphenidate is added as a solution in ethyl acetate mixed together with the polyacrylate. After removal of volatile process solvents, the formulation is transferred to a coating operation where it is coated onto a protective release liner at a controlled specific thickness. The coated product is then passed through an oven in order to drive off all volatile processing solvents. The dried product on the release liner is then joined to the backing material and wound onto rolls. Appropriate size and shape dosage units are die-cut from the roll material and then pouched.

TABLE 13

| Ingredients | Amount (%) |
|---|---|
| polysiloxane (Dow CorningSilicone Adhesive X7-4919) | 42.8 |
| polyacrylate (National Starch Acrylic Adhesive, Duro-Tak 80-1194) | 28.6 |
| polydimethylsiloxane fluid (Dow Corning 360 medical fluid) | 2.5 |
| lecithin | 1.3 |
| propylene glycol | 1.0 |
| dipropylene glycol | 1.0 |
| oleic acid | 0.8 |
| methylphenidate base | 20.0 |
| sucrose octaacetate | 1.0 |
| tartrazine | 1.0 |

ADVANTAGES OF THE INVENTION

The present invention provides a combination of three effective approaches to reduce the abuse potential for dosage forms of psychoactive drugs. Bittering agents, dye indicators and/or fine particulate matter are added to dosage forms of prescription psychoactive drug formulations to reduce the abuse potential of the drug formulations. The bittering agents and dye indicators may be incorporated into deterrent beads having a barrier coating. The beads can be fabricated separately from the manufacturing of the pharmaceutical dosage form of reduced abuse potential. Such "universal" deterrent beads can shorten product development time and minimize the impact of the bittering agents/dye indicators on product performance. The deterrent beads can also be formulated so that the bittering agents/dye indicators are not released under normal administration conditions to minimize possible adverse effects from these agents.

What is claimed is:

1. A pharmaceutical formulation having a decreased abuse potential comprising particles, wherein each particle comprises:
   (a) drug-free granules, beads or mini-tablets comprising at least one bittering agent selected from the group consisting of sugar octaacetate, denatonium benzoate, denatonium saccharide, caffeine, quinine or a quinine salt, bitter orange peel oil, pepper extract and capsicum;
   (b) a first pharmaceutically acceptable coating atop the drug-free granules, beads or mini-tablets that does not dissolve in a gastro-intestinal tract, such that the bittering agent is not released in a human body when the formulation is properly administered;
   (c) a second pharmaceutically acceptable coating atop the first coating consisting essentially of an active pharmaceutical ingredient (API) selected from the group consisting of opioids, central nerve system (CNS) depressants and stimulants; and
   (d) a third pharmaceutically acceptable coating atop the second coating, the third coating comprising an enteric coating, a sustained release coating, or both.

2. The formulation of claim 1, further comprising at least one abuse deterrent indicator dye.

3. The formulation of claim 1, further comprising a fine insoluble particulate matter.

4. The pharmaceutical formulation of claim 3, wherein the fine insoluble particulate matter is selected from the group consisting of polycarbophil, methacrylic acid copolymer, microcrystalline cellulose, sodium starch glycolate, crospovidone, croscarmellose sodium, talcum, silicon dioxide, and combinations thereof.

5. The pharmaceutical formulation of claim 3, wherein the fine insoluble particulate matter has a particle size of from 1 μm to 150 μm.

6. The pharmaceutical formulation of claim 1, wherein the first coating comprises cellulose acetate, cellulose acetate butyrate, cellulose acetate propionate, ethyl cellulose, poly(ethyl acrylate), poly(methyl methacrylate), poly(trimethylammonioethylmethacrylate chloride), or a combination thereof.

7. The pharmaceutical formulation of claim 1 in the form of capsules, tablets, and/or liquid suspensions.

8. A method of reducing a potential for abuse of a formulation of a psychoactive drug by a subject, comprising administering to the subject a pharmaceutical formulation according to claim 1.

9. A dosage form having reduced abuse potential comprising particles, wherein each particle comprises:
   (a) drug-free granules, beads or mini-tablets comprising at least one bittering agent selected from the group consisting of sugar octaacetate, denatonium benzoate, denatonium saccharide, caffeine, quinine or a quinine salt, bitter orange peel oil, pepper extract and capsicum;
   (b) a first pharmaceutically acceptable coating atop the drug-free granules, beads or mini-tablets that does not dissolve in a gastro-intestinal tract, such that the bittering agent is not released in a human body when the formulation is properly administered;
   (c) a second pharmaceutically acceptable coating atop the first coating consisting essentially of an active pharmaceutical ingredient (API) selected from the group consisting of opioids, central nerve system (CNS) depressants and stimulants,
   wherein the dosage form is selected from the group consisting of capsules, and liquid suspensions.

10. The dosage form of claim 9, further comprising at least one abuse deterrent indicator dye.

11. The dosage form of claim 9, further comprising a fine insoluble particulate matter.

12. The dosage form of claim 11, wherein the fine insoluble particulate matter is selected from the group consisting of polycarbophil, methacrylic acid copolymer, microcrystalline cellulose, sodium starch glycolate, crospovidone, croscarmellose sodium, talcum, silicon dioxide, and combinations thereof.

13. The dosage form of claim 11, wherein the fine insoluble particulate matter has a particle size of from 1 μm to 150 μm.

14. The dosage form of claim 9, wherein the first coating comprises cellulose acetate, cellulose acetate butyrate, cellulose acetate propionate, ethyl cellulose, poly(ethyl acrylate), poly(methyl methacrylate), poly(trimethylammonioethylmethacrylate chloride), or a combination thereof.

15. A method of reducing a potential for abuse of a formulation of a psychoactive drug by a subject, comprising administering to the subject a dosage form according to claim 9.

* * * * *